United States Patent [19]

Smith et al.

[11] Patent Number: 5,693,861
[45] Date of Patent: Dec. 2, 1997

[54] PROCESS FOR PREPARING SOLID AMINE OXIDES

[75] Inventors: Rebecca F. Smith; Y.-D. Mark Chen; R. Woodrow Wilson, Jr., all of Baton Rouge; Mayur P. Shah, Kenner, all of La.; Kim R. Smith, Huntington, Ind.; Sharon B. McGee, Baton Rouge, La.

[73] Assignee: Albemarle Corporation, Richmond, Va.

[21] Appl. No.: 78,500

[22] Filed: Jun. 21, 1993

Related U.S. Application Data

[63] Continuation of Ser. No. 939,812, Sep. 3, 1992, abandoned, which is a continuation-in-part of Ser. No. 740,063, Aug. 5, 1991, abandoned, and a continuation-in-part of Ser. No. 740,409, Aug. 5, 1991, abandoned.

[51] Int. Cl.$^6$ .................................................. C07C 291/00
[52] U.S. Cl. .................................................. 564/298
[58] Field of Search .................................................. 564/298

[56] References Cited

U.S. PATENT DOCUMENTS

| | | | |
|---|---|---|---|
| 4,795,594 | 1/1989 | Darkowski | 260/502 R |
| 4,889,954 | 12/1989 | Laurenzo et al. | 564/298 |
| 4,960,934 | 10/1990 | Smith et al. | 564/298 |
| 5,130,488 | 7/1992 | Smith et al. | 564/298 |

FOREIGN PATENT DOCUMENTS

| | | |
|---|---|---|
| 0094560 | 11/1983 | European Pat. Off. . |
| 0401503 | 12/1990 | European Pat. Off. . |

*Primary Examiner*—Peter O'Sullivan
*Attorney, Agent, or Firm*—Philip M. Pippenger

[57] ABSTRACT

A highly pure, white, solid amine oxide is prepared in high yield with minimal decomposition of the solvent by (A) reacting a tert-amine with a 15–20% stoichiometric excess of concentrated hydrogen peroxide at 50°–55° C. in the presence of controlled amounts of carbon dioxide and ethyl acetate until the reaction mixture contains 35–45 % by weight of ethyl acetate and less than 0.8% by weight of unreacted amine, (B) catalytically decomposing residual hydrogen peroxide, (C) separating the reaction mixture from the decomposition catalyst, (D) cooling the reaction mixture to 0° C. to form a slurry, (E) centrifuging the slurry to separate the amine oxide, and (F) vacuum drying the amine oxide at ambient temperature—the reaction mixture being diluted to an amine oxide content of 25–30% by weight with additional ethyl acetate or a mixture thereof with a co-solvent, such as a low-boiling n-alkane, after the completion of Step A and prior to the beginning of Step D.

4 Claims, No Drawings

PROCESS FOR PREPARING SOLID AMINE OXIDES

CROSS-REFERENCE TO RELATED APPLICATIONS

This application is a continuation of application Ser. No. 07/939,812, filed Sep. 3, 1992, now abandoned, which is a continuation-in-part of application Ser. Nos. 07/740,063 and 07/740,404, both filed 5 Aug. 1991 and now abandoned.

FIELD OF INVENTION

The invention relates to a process for preparing and recovering solid amine oxides.

BACKGROUND

It is known that solid amine oxides have advantages over amine oxide solutions in that they can be transported more economically and can be used in formulations which could not tolerate the presence of the water or other solvent in which amine oxides are conventionally prepared.

As disclosed in U.S. Pat. No. 5,130,488 (Smith et al.), solid amine oxides can be prepared by reacting a tert-amine with hydrogen peroxide in the presence of ethyl acetate and cooling to precipitate the product. This process is superior to previously-known methods of preparing amine oxides. However, its use can sometimes lead to cleavage of the solvent, plating on the walls of the vessel used for the precipitation, contamination of the product with residual peroxide, and/or discoloration of the product.

SUMMARY OF INVENTION

It has been found that improved results can be achieved when an amine oxide is prepared by a high solids process in which (A) a tert-amine oxide is reacted at 50°–55° C. with a 15–20% stoichiometric excess of an aqueous hydrogen peroxide having a concentration of 50–90% by weight in the presence of carbon dioxide and ethyl acetate, the amount of carbon dioxide in the reaction mixture being maintained at a level not higher than 0.2% by weight and the ethyl acetate being gradually added to the reaction mixture during the course of the reaction until it constitutes 35–45% of the weight of the reaction mixture, (B) the reaction is continued until the reaction mixture contains less than 0.8% by weight unreacted amine, (C) the resultant reaction mixture is contacted with a peroxide decomposition catalyst to decompose residual hydrogen peroxide, additional ethyl acetate or a mixture thereof with a co-solvent being added before, during, or after the decomposition treatment to dilute the reaction mixture to an amine oxide content of 25–30% by weight, (D) the reaction mixture is then separated from the catalyst and cooled to about 0° C. to form a slurry, (E) the slurry is centrifuged to separate the amine oxide, and (F) the amine oxide is vacuum dried at ambient temperature.

DETAILED DESCRIPTION

The amine which is oxidized in the process may be any of the amines conventionally used in such processes. As is known, these amines include a variety of tert-amines corresponding to the formula RR'R"N wherein R, R', and R" are independently selected from alkyl, hydroxyalkyl, cycloalkyl, and aralkyl groups containing up to 30 carbons and any two of those groups may form a non-aromatic heterocyclic group, such as a morpholine or piperidine ring, with the nitrogen. However, they are generally tert-amines of that formula in which R, R', and R" are independently selected from primary alkyl and hydroxyalkyl groups containing 1–30 carbons.

Because of greater interest in the oxides prepared from them, the tert-amines which are apt to be preferred for use in the process are those in which R is methyl, ethyl, or hydroxyethyl; R' is a primary alkyl group containing 6–20 carbons; and R" is independently selected from methyl, ethyl, hydroxyethyl, and primary alkyl groups containing 6–20 carbons.

Exemplary of the tert-amines that may be used are trimethylamine, triethylamine, N-isobutyldimethylamine, trihexylamine, N,N-dimethyl-2-ethylhexylamine-N-eicosyldimethylamine, N-isobutyl-N-triacontylmethylamine, N-benzyldimethylamine, N-ethyldibenzylamine, N,N-diisobutyl-4-t-butylbenzylamine, tri-2-hydroxyethylamine, and, more preferably, (1) the N-alkyldimethyl- and N,N-dialkylmethylamines in which the alkyl groups are hexyl, octyl, decyl, dodecyl, tetradecyl, hexadecyl, octadecyl, and/or eicosyl, (2) the corresponding amines in which the methyl groups are replaced with ethyl or hydroxyethyl groups, and (3) mixtures of such amines.

As already mentioned, the aqueous hydrogen peroxide which is reacted with the tert-amine may have a concentration of 50–90% by weight. A solution having a concentration of about 70% is generally preferred to facilitate the formation of a final reaction mixture from which the amine oxide dihydrate-containing products of Smith et al. can be precipitated. However, even when such products are desired, it is not necessary to employ a 70% hydrogen peroxide as a reactant. As taught by Smith et al., the water/amine oxide mol ratio can be adjusted at the end of the reaction, when necessary, to provide the $\leq 2.1/1$ ratio that leads to the precipitation of an amine oxide dihydrate-containing product.

It is important to employ a 15–20% stoichiometric excess of hydrogen peroxide in order to achieve a high conversion of amine to amine oxide and higher reaction rates while avoiding discoloration of the product.

As in the preferred Smith et al. process, the process of the invention is conducted in the presence of carbon dioxide to increase the reaction rate. However, the present process differs in one important respect from the Smith et al. process and other known amine oxide syntheses which were developed when all that was believed to be important about the amount of carbon dioxide used was the total amount employed during the reaction. In those processes, it is permissable, e.g., to introduce all of the carbon dioxide initially or to maintain a constant flow of carbon dioxide to the reactor such that its concentration in the reaction mixture varies from a relatively high level at the beginning of the reaction to a relatively low level at the end of the reaction. In fact, the carbon dioxide-promoted amine oxide syntheses have conventionally been conducted in such a manner; and it has frequently been preferred to employ fairly large amounts of carbon dioxide to maximize its promotional effect. In the present process, on the other hand, it is required that the concentration of carbon dioxide in the reaction mixture be maintained at a level of $\leq 0.2\%$ by weight throughout the reaction in order to avoid discoloration of the product. This control of the carbon dioxide concentration may be achieved in any suitable way, e.g., by bubbling the carbon dioxide through the reactor at a variable rate.

Ethyl acetate is used, as in Smith et al., to maintain stirrability of the reaction mixture throughout the reaction while forming a product that can be easily recovered from the reaction mixture.

The process is preferably conducted by (1) charging the tert-amine to a reactor which has been passivated with nitric acid to prevent decomposition of hydrogen peroxide during the reaction, (2) adding any chelating agent (e.g., diethylenetriaminepentaacetic acid or ethylenediaminetetraacetic acid) which it might be desired to use, (3) initiating the controlled bubbling of carbon dioxide through the reaction mixture, (4) heating the reactor to 50°–55° C., preferably 50° C., to provide conditions suitable for effecting reaction at a reasonable rate while minimizing cleavage of the solvent, (5) slowly adding the hydrogen peroxide to the stirred contents of the reactor at a rate such as to permit temperature control while slowly adding the ethyl acetate until it constitutes 35–45% by weight of the reaction mixture, and (6) continuing the reaction at 50°–55° C. until the reaction mixture contains <0.8%, preferably <0.5% by weight of unreacted amine.

When the reaction has been completed, the reaction mixture is contacted with a peroxide decomposition catalyst, such as palladium, ferrous sulfate, montmorillonite, activated charcoal, or —preferably—the manganese dioxide of U.S. Pat. No. 4,889,954 (Laurenzo et al.), to decompose residual hydrogen peroxide. This contact could be achieved by adding the decomposition catalyst to the reaction vessel and agitating the mixture to insure good contact between the catalyst and the hydrogen peroxide. However, for commercial operations, it is preferred to use a separate vessel containing a bed or slurry of the decomposition catalyst.

In a preferred embodiment of the invention, (1) the mixture obtained from the tert-amine/hydrogen peroxide reaction, (2) ethyl acetate or a mixture thereof with a co-solvent, and (2) manganese dioxide or other decomposition catalyst are added to a separate vessel which, like the reactor, is maintained at 50°–55° C.; and the ingredients are kept in contact with one another until the hydrogen peroxide content has been reduced to the desired degree, generally to a level <0.2% by weight.

Dilution of the reaction mixture to an amine oxide content of 25–30% by weight with ethyl acetate or a mixture thereof with a co-solvent may be accomplished before, during, or after the decomposition treatment, depending on when it is most convenient to add more solvent. All that is actually required is that this dilution be effected prior to crystallization of the amine oxide, preferably prior to separating the reaction mixture from the decomposition catalyst, in order to promote fluidity of the crystallization slurry.

When the hydrogen peroxide content of the reaction mixture has been reduced to the desired degree, the reaction mixture and decomposition catalyst are separated, e.g., by pressuring the contents of the vessel in which the decomposition was accomplished through a cartridge filter. Crystallization of the amine oxide is then effected by cooling the diluted reaction mixture to about 0° C., preferably by vacuum cooling or evaporative cooling in a jacketed vessel.

Satisfactory results can be achieved when ethyl acetate is the only organic solvent in the diluted reaction mixture which is cooled in the vessel used for the crystallization. However, since the use of ethyl acetate as the sole solvent sometimes leads to plating of the product on the walls of the vessel, it is frequently desirable to utilize the ethyl acetate in conjunction with a co-solvent, such as a low-boiling n-alkane, to prevent or minimize this plating.

When a low-boiling alkane, i.e., pentane, hexane, or heptane, is employed to prevent or minimize plating on the walls of the crystallization vessel, it is used in an amount such as to provide an ethyl acetate/alkane weight ratio of about 0.75/1 to 4/1—a ratio that may be obtained by adding an appropriate amount of an alkane or a suitably proportionated alkane/ethyl acetate mixture to the product already containing the ethyl acetate utilized during the reaction. The n-alkane which is preferred as the diluent can depend on the use planned for the solvent after the amine oxide has been crystallized therefrom. Each is satisfactory when the solvent is to be discarded, but pentane is the most easily separated from ethyl acetate and therefore preferred when reuse of the ethyl acetate is intended.

The product of the crystallization step is a slurry containing precipitated amine oxide. This slurry is centrifuged to separate a wet amine oxide cake containing <25% moisture from the solvent. After being separated by centrifugation, the amine oxide cake is vacuum dried at ambient temperature; and the ethyl acetate, after being separated from any contaminants, such as water, ethanol, and/or co-solvents, may be recycled to the reactor if desired.

The invention is advantageous in that it is an economical process for providing a highly pure, white, solid amine oxide in high yield with minimal decomposition of the solvent and maximum protection of the equipment used.

The following examples are given to illustrate the invention and are not intended as a limitation thereof.

EXAMPLE 1

Part A

Charge a suitable reaction vessel with 500 g (2.07 mols) of N-tetradecyldimethylamine and 1.2g (3.05 mmols) of diethylenetriaminepentaacetic acid. Stir the mixture at 50° C. and begin bubbling carbon dioxide through the vessel at a variable rate so as to maintain a constant concentration of 0.1% by weight of carbon dioxide in the reaction mixture. While bubbling carbon dioxide and stirring the reaction mixture, add 465 mL (419.43 g) of ethyl acetate dropwise over a period of 33 minutes and add 120 g (2.47 mols) of 70% aqueous hydrogen peroxide dropwise during the first 10 minutes of that period. Continue heating the stirred reaction mixture for another ten hours and then terminate the charge of carbon dioxide to the vessel. NMR analysis of the product mixture shows 99.5% amine conversion.

Part B

Charge the product mixture of Part A, 100 mL (90.2 g) of ethyl acetate, and 130 mL (85.7 g) of n-hexane to an agitated vessel maintained at 50°–55° C. and containing manganese dioxide powder. Stir the mixture, sampling every 30 minutes, until the hydrogen peroxide content is ≦0.1% by weight. Then transfer the contents of the vessel through a filter into a crystallization vessel, and cool to 0° C. with jacketed cooling to provide a slurry precipitated amine oxide. There is no plating of the vessel walls during crystallization.

Part C

Centrifuge the slurry of Part B to separate a wet amine oxide cake containing <25% moisture from the solvent, and remove the remainder of the volatile solvent from the cake by vacuum drying at ambient temperature. The product is a white solid which analysis shows to be N-tetradecyldimethylamine oxide dihydrate containing <0.3% residual amine, <0.3% hydrogen peroxide, and <0.5% acetic acid.

EXAMPLE 2

Repeat Example 1 except for replacing the 85.7 g of n-hexane with an equal amount of ethyl acetate in the charge to the peroxide decomposition vessel. Then repeat the process for a total of ten runs. Similar results are observed except that there is some plating on the walls of the crystallization vessel during some of the runs.

EXAMPLE 3

Repeat Example 1 except for changing the rate at which carbon dioxide is bubbled through the reactor so that its concentration in the reaction mixture gradually increases to a maximum of 0.1% by weight. Similar results are observed except that the reaction time must be extended to 12 hours to approach the 99.5% conversion of Example 1.

EXAMPLE 4

Repeat Example 1 except for changing the rate at which carbon dioxide is bubbled through the reactor so that its concentration in the reaction mixture is allowed to vary between a minimum of 0.1% and a maximum of ~0.2% by weight during the reaction. Similar results are observed except that a shorter time (6–8 hours) is required to reach complete conversion of the amine to the amine oxide.

COMPARATIVE EXAMPLE A

Repeat Example 1 except for allowing the concentration of carbon dioxide in the reaction mixture to vary between 0.2% and 0.5% by weight during the reaction. The product is orange rather than white.

COMPARATIVE EXAMPLE B

Repeat Example 1 except for allowing the concentration of carbon dioxide in the reaction mixture to increase from 0.1% to 0.4% before slowing its feed rate during the reaction. The product is orange.

COMPARATIVE EXAMPLE C

Repeat Example 1 except for conducting the reaction at 75° C. instead of 50° C. The reaction is faster, but the product contains 1.4% by weight of acetic acid resulting from increased cleavage of ethyl acetate at the higher temperature.

What is claimed is:

1. In a high solids process for preparing an amine oxide by the carbon dioxide-promoted reaction of a tert-amine with a 15–20% stoichiometric excess of an aqueous hydrogen peroxide having a concentration of 50–90% by weight in the presence of an amount of ethyl acetate sufficient to maintain the reaction mixture stirrable throughout the reaction, the improvement which comprises avoiding discoloration of the product by introducing the carbon dioxide at a variable rate during the reaction so that its concentration in the reaction mixture does not exceed 0.2% by weight at any time throughout the reaction, the total amount of carbon dioxide promoter employed being about 0.1–0.2%, based on the weight of the reaction mixture.

2. The process of claim 1 wherein the tert-amine is a compound corresponding to the formula RR'R"N in which R,R', and R" are independently selected from primary alkyl and hydroxyalkyl groups containing 1–30 carbons.

3. The process of claim 2 wherein R is methyl, ethyl, or hydroxyethyl; R' is a primary alkyl group containing 6–20 carbons; and R" is independently selected from methyl, ethyl, hydroxyethyl, and primary alkyl groups containing 6–20 carbons.

4. The process of claim 3 wherein R and R" are methyl.

\* \* \* \* \*